United States Patent
Saraf et al.

(10) Patent No.: US 12,163,938 B2
(45) Date of Patent: *Dec. 10, 2024

(54) COMPACT HUMIDITY AND PRESSURE SENSOR WITH TEMPERATURE CONTROL

(71) Applicant: Murata Manufacturing Co., Ltd., Kyoto (JP)

(72) Inventors: Vivek Saraf, Austin, TX (US); Vishnu Srinivasan, Austin, TX (US)

(73) Assignee: Murata Manufacturing Co., Ltd., Nagaokakyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/453,137

(22) Filed: Aug. 21, 2023

(65) Prior Publication Data

US 2024/0044857 A1 Feb. 8, 2024

Related U.S. Application Data

(63) Continuation of application No. 17/195,027, filed on Mar. 8, 2021, now Pat. No. 11,761,936.
(Continued)

(51) Int. Cl.
*G01N 27/22* (2006.01)
*G01K 7/20* (2006.01)
(Continued)

(52) U.S. Cl.
CPC ........... *G01N 33/0031* (2013.01); *G01K 7/20* (2013.01); *G01L 19/0092* (2013.01);
(Continued)

(58) Field of Classification Search
CPC ............ G01K 7/16; G01K 7/18; G01K 7/183; G01K 7/186; G01K 7/20; G01K 7/203;
(Continued)

(56) References Cited

U.S. PATENT DOCUMENTS 4,749,889 A 6/1988 Lagoni et al.
5,098,196 A 3/1992 O'Neill
(Continued)

FOREIGN PATENT DOCUMENTS

DE 10335553 2/2005
EP 1615337 1/2006
(Continued)

OTHER PUBLICATIONS pSEMI Corporation, Response filed in the USPTO dated Apr. 12, 2019 for U.S. Appl. No. 15/908,469, 12 pgs.
(Continued)

*Primary Examiner* — Herbert K Roberts
(74) *Attorney, Agent, or Firm* — Steinfl + Bruno LLP

(57) ABSTRACT

Novel integrated circuit environmental and temperature sensors in combination with measurement circuitry fully integrated as part of an ASIC die, which may be co-packaged with a pressure sensor integrated circuit to create a compact yet sensitive environment monitoring product. Embodiments may include one or more integrated local heating elements and control circuitry that are power supply independent, make efficient use of battery power, include an accurate in-built temperature detection capability, and provide digital close-loop control of the heating elements.

17 Claims, 7 Drawing Sheets

Related U.S. Application Data

(60) Provisional application No. 62/987,245, filed on Mar. 9, 2020.

(51) Int. Cl.
  *G01L 19/00* (2006.01)
  *G01L 19/04* (2006.01)
  *G01N 33/00* (2006.01)
  *H01L 23/34* (2006.01)

(52) U.S. Cl.
  CPC ......... *G01N 27/223* (2013.01); *G01N 27/227* (2013.01); *H01L 23/345* (2013.01)

(58) Field of Classification Search
  CPC ............ G01K 7/206; G01K 7/21; G01K 7/22; G01K 7/223; G01K 7/226; G01K 7/24; G01K 7/245; G01K 7/25; G01K 7/26; G01K 7/28; G01K 2007/163; G01K 2007/166; G01N 27/223; G01N 27/227; G01L 19/0092; G01L 19/04
  See application file for complete search history.

(56) References Cited

U.S. PATENT DOCUMENTS

| | | |
|---|---|---|
| 6,297,696 B1 | 10/2001 | Abdollahian et al. |
| 6,392,490 B1 | 5/2002 | Gramegna et al. |
| 6,731,171 B2 | 5/2004 | Yamashita |
| 6,804,502 B2 | 10/2004 | Burgener et al. |
| 6,831,504 B1 | 12/2004 | Holloway et al. |
| 7,248,120 B2 | 7/2007 | Burgener et al. |
| 7,276,976 B2 | 10/2007 | Oh et al. |
| 7,649,418 B2 | 1/2010 | Matsui |
| 7,656,233 B2 | 2/2010 | Lee |
| 7,737,790 B1 | 6/2010 | Chen et al. |
| 7,859,243 B2 | 12/2010 | Lorenz |
| 7,910,993 B2 | 3/2011 | Brindle et al. |
| 8,022,755 B2 | 9/2011 | Gomez |
| 8,487,706 B2 | 7/2013 | Li et al. |
| 8,554,389 B2 | 10/2013 | Cox |
| 9,083,287 B2 | 7/2015 | Papamichail |
| 9,148,088 B1 | 9/2015 | Ding |
| 9,164,052 B1 | 10/2015 | Speer et al. |
| 9,178,493 B1 | 11/2015 | Nobbe |
| 9,219,445 B2 | 12/2015 | Nobbe et al. |
| 9,231,528 B2 | 1/2016 | Granger-Jones |
| 9,276,527 B2 | 3/2016 | Gaynor |
| 9,294,056 B2 | 3/2016 | Nobbe et al. |
| 9,331,643 B2 | 5/2016 | Gaynor |
| 9,413,298 B2 | 8/2016 | Nobbe et al. |
| 9,419,565 B2 | 8/2016 | Nobbe et al. |
| 9,503,026 B2 | 11/2016 | Lam et al. |
| 9,509,263 B2 | 11/2016 | Lam |
| 9,595,923 B2 | 3/2017 | Nobbe et al. |
| 9,602,063 B2 | 3/2017 | Kaatz et al. |
| 9,641,141 B1 | 5/2017 | Zheng et al. |
| 9,647,631 B2 | 5/2017 | Gaynor |
| 9,837,965 B1 | 12/2017 | Wagh et al. |
| 9,843,293 B1 | 12/2017 | Wagh et al. |
| 9,874,893 B2 | 1/2018 | Ciubotaru |
| 9,882,531 B1 | 1/2018 | Willard et al. |
| 10,056,874 B1 | 8/2018 | Ranta et al. |
| 10,250,199 B2 | 4/2019 | Klaren et al. |
| 10,305,433 B2 | 5/2019 | Ranta et al. |
| 10,439,562 B2 | 10/2019 | Tokuda et al. |
| 10,439,563 B2 | 10/2019 | Takagi et al. |
| 11,761,936 B2 | 9/2023 | Saraf et al. |
| 11,977,044 B2 | 5/2024 | Saraf |
| 2002/0074499 A1 | 6/2002 | Butler |
| 2003/0137355 A1 | 7/2003 | Lin |
| 2005/0029453 A1 | 2/2005 | Allen et al. |
| 2006/0210427 A1 | 9/2006 | Theil |
| 2008/0284519 A1 | 11/2008 | Andrews |
| 2009/0015316 A1 | 1/2009 | Song et al. |
| 2009/0258611 A1 | 10/2009 | Nakamura et al. |
| 2011/0125204 A1 | 5/2011 | Louise |
| 2011/0226041 A1 | 9/2011 | Cummins |
| 2011/0279178 A1 | 11/2011 | Outaleb et al. |
| 2011/0298538 A1 | 12/2011 | Andrys et al. |
| 2012/0168882 A1 | 7/2012 | Cherian |
| 2013/0139587 A1 | 6/2013 | Le Neel |
| 2013/0222075 A1 | 8/2013 | Reedy et al. |
| 2013/0229231 A1 | 9/2013 | Tanaka et al. |
| 2014/0097698 A1 | 4/2014 | Wang et al. |
| 2014/0184335 A1 | 7/2014 | Nobbe et al. |
| 2014/0184337 A1 | 7/2014 | Nobbe et al. |
| 2014/0216153 A1 | 8/2014 | Pion |
| 2014/0266460 A1 | 9/2014 | Nobbe et al. |
| 2014/0291677 A1 | 10/2014 | Le Neel et al. |
| 2015/0077185 A1 | 3/2015 | Ding et al. |
| 2015/0077187 A1 | 3/2015 | Lam et al. |
| 2015/0270806 A1 | 9/2015 | Wagh et al. |
| 2015/0326206 A1 | 11/2015 | Nobbe |
| 2015/0326326 A1 | 11/2015 | Nobbe et al. |
| 2016/0347606 A1 | 12/2016 | Bruno |
| 2017/0194916 A1 | 7/2017 | Whittaker et al. |
| 2018/0083578 A1 | 3/2018 | Klaren |
| 2018/0115287 A1 | 4/2018 | Rabjohn et al. |
| 2018/0262163 A1 | 9/2018 | Tokuda et al. |
| 2018/0262164 A1 | 9/2018 | Ranta et al. |
| 2018/0262166 A1 | 9/2018 | Takagi et al. |
| 2018/0316327 A1 | 11/2018 | Ranta et al. |
| 2019/0173433 A1 | 6/2019 | Ranta et al. |
| 2021/0278385 A1 | 9/2021 | Saraf et al. |
| 2022/0260515 A1 | 8/2022 | Saraf |

FOREIGN PATENT DOCUMENTS

| | | | |
|---|---|---|---|
| EP | 3124937 A1 * | 2/2017 | ........... G01L 9/0072 |
| WO | 2009108391 | 9/2009 | |
| WO | 2012/082445 | 6/2012 | |
| WO | 2017122178 | 7/2017 | |
| WO | 2018160771 | 9/2018 | |

OTHER PUBLICATIONS

Nguyen, Hieu P., Office Action received from the USPTO dated Sep. 14, 2018 for U.S. Appl. No. 15/908,354, 19 pgs.
Fakhruddin, Asm Nmn, Office Action received from the USPTO dated Sep. 28, 2023 for U.S. Appl. No. 17/176,972, 19 pgs.
Fakhruddin, Asm Nmn, Notice of Allowance received from the USPTO dated Jan. 4, 2024 for U.S. Appl. No. 17/176,972, 13 pgs.
pSEMI Corporation, Preliminary Amendment filed in the USPTO dated Apr. 26, 2021 for U.S. Appl. No. 17/176,972, 6 pgs.
pSEMI Corporation, Response filed in the USPTO dated Nov. 29, 2022 for U.S. Appl. No. 17/176,972, 8 pgs.
pSEMI Corporation, Response filed in the USPTO dated Aug. 2, 2023 for U.S. Appl. No. 17/176,972, 10 pgs.
pSEMI Corporation, Response filed in the USPTO dated Aug. 2, 2023 for U.S. Appl. No. 17/176,972, 13 pgs.
pSEMI Corporation, Response filed in the USPTO dated Jan. 30, 2023 for U.S. Appl. No. 17/195,027, 8 pgs.
pSEMI Corporation, Response filed in the USPTO dated Apr. 25, 2023 for U.S. Appl. No. 17/195,027, 11 pgs.
Dai, et al., "A Capacitive Humidity Sensor Intregrated with Micro Heater and Ring Oscillator Circuit Fabricated by CMOS-MEMS Technique", Sensors and Actuators B: Chemical, Elsevier BV, NL, vol. 122, No. 2, Mar. 15, 2007, pp. 375-380.
Niedermeyr, Gabriela, Invitation to Pay Additional Fees received from the EPO dated May 28, 21 for appln. No. PCT/US2021/021385, 14 pgs.
Igarashi, et al., "A Cryostat and Temperature Control System Optimized for Measuring Relaxations of Glass-Forming Liquids", Review of Scientific Instruments, AIP, Melville, NY, US, vol. 79, No. 4, Apr. 11, 2008, p. 45105.
Bota, et al., "A Monolithic Interface Circuit for Gas Sensor Arrays: Control and Measurement", Analog Integrated Circuits and Signal Processing, Kluwer Academic Publishers, BO, vol. 40, No. 2, Aug. 1, 2004, pp. 175-184.

(56) References Cited

OTHER PUBLICATIONS

Minco, "CT298 HeaterStat Temperature Controller",, URL:https://www.minco.com/wp-content/uploads/CT298-User-Guide.pdf, Jan. 1, 14, pp. 1-12.
Stussi, Elisa, International Search Report and Written Opinion received from the EPO dated Aug. 23, 21 for appln. No. PCT. US2021/021385, 22 pgs.
Fakhruddin, Asm Nmn, Office Action received from the USPTO dated Sep. 9, 2022 for U.S. Appl. No. 17/176,972, 26 pgs.
Fakhruddin, Asm Nmn, Final Office Action received from the USPTO dated May 2, 23 for U.S. Appl. No. 17/176,972, 27 pgs.
Roberts, Herbert K., Office Action received from the USPTO dated Dec. 5, 2022 for U.S. Appl. No. 17/195,027, 7 pgs.
Roberts, Herbert K., Office Action received from the USPTO dated Feb. 13, 2023 for U.S. Appl. No. 17/195,027, 37 pgs.
Roberts, Herbert K., Notice of Allowance received from the USPTO dated May 9, 2023 for U.S. Appl. No. 17/195,027, 11 pgs.
Fakhruddin, Asm Nmn, Final Office Action received from the USPTO dated Sep. 28, 2023 for U.S. Appl. No. 17/176,972, 19 pgs.
Nguyen, Hieu P., Office Action received from the USPTO dated Jan. 30, 2018 for U.S. Appl. No. 15/445,811, 6 pgs.
Nguyen, Hieu P., Notice of Allowance received from the USPTO dated May 23, 2018 for U.S. Appl. No. 15/445,811, 22 pgs.
Nguyen, Lee, Notice of Allowance received from the USPTO dated Jul. 31, 2017 for U.S. Appl. No. 14/272,415, 13 pgs.
Nguyen, Hieu P., Notice of Allowance received from the USPTO dated Apr. 2, 2019 for U.S. Appl. No. 15/908,533, 16 pgs.
Nguyen, Hieu P., Office Action received from the USPTO dated Jan. 7, 2019 for U.S. Appl. No. 15/908,533, 27 pgs.
Nguyen, Hieu P., Office Action received from the USPTO dated Oct. 12, 2018 for U.S. Appl. No. 15/908,533, 6 pgs.
Gundlach, Susanne, Invitation to Pay Additional Fees and, Where Applicable, Protest Fee received from the EPO dated Jun. 15, 2018 for appln. No. PCT/US2018/020332, 13 pgs.
Mouanda, Thierry, International Search Report and Written Opinion received from the EPO dated Sep. 21, 2018 for appln. No. PCT/US2018/020332, 21 pgs.
Peregrine Semiconductor Corporation, Amendment filed in the EPO dated Nov. 21, 2018 for appln. No. PCT/US2018/020332, 57 pgs.
Nguyen, Hieu P., Notice of Allowance received from the USPTO dated May 30, 2019 for U.S. Appl. No. 15/908,354, 29 pgs.
pSEMI Corporation, Preliminary Amendment filed in the USPTO dated May 29, 2018 for U.S. Appl. No. 15/908,354, 7 pgs.
pSEMI Corporation, Response filed in the USPTO dated Oct. 30, 2018 for U.S. Appl. No. 15/908,354, 10 pgs.
Ranta, et al., Preliminary Amendment filed in the USPTO dated Oct. 16, 2017 for U.S. Appl. No. 15/445,811, 20 pgs.
Ranta, et al., Response filed in the USPTO dated Feb. 9, 2018 for U.S. Appl. No. 15/445,811, 10 pgs.
Nguyen, Patricia T., Office Action received from the USPTO dated Dec. 11, 2017 for U.S. Appl. No. 15/268,229, 6 pgs.
Nguyen, Patricia T., Office Action received from the USPTO dated May 3, 2018 for U.S. Appl. No. 15/268,229, 34 pgs.
Klaren, et al., Preliminary Amendment filed in the USPTO dated Nov. 29, 2016 for U.S. Appl. No. 15/268,229, 11 pgs.
Klaren, et al., Response filed in the USPTO dated Jan. 29, 2018 for U.S. Appl. No. 15/268,229, 7 pgs.
Klaren, et al., Response filed in the USPTO dated Jul. 17, 2018 for U.S. Appl. No. 15/268,229, 10 pgs.
Wienema, David, International Search Report and Written Opinion received from the EPO dated Aug. 31, 2017 for appln. No. PCT/US2017/044015, 19 pgs.
Nguyen, Hieu P., Office Action received from the USPTO dated Sep. 14, 2018 for U.S. Appl. No. 15/908,469, 18 pgs.
Nguyen, Hieu P., Office Action received from the USPTO dated Nov. 9, 2018 for U.S. Appl. No. 16/025,873, 5 pgs.
Nguyen, Hieu P., Final Office Action received from the USPTO dated Jan. 14, 2019 for U.S. Appl. No. 15/908,469, 17 pgs.
Nguyen, Hieu P., Office Action received from the USPTO dated Feb. 15, 2019 for U.S. Appl. No. 16/025,873, 18 pgs.
Mouanda, Thierry, Invitation to Restrict or Pay Additional Fees, and, Where Applicable, Protest Fee received from the EPO dated Mar. 5, 2019 for appln. No. PCT/US2018/020332, 4 pgs.
Mouanda, Thierry, Written Opinion received from the EPO dated May 15, 2019 for appln. No. PCT/US2018/020332, 8 pgs.
Nguyen, Hieu P., Notice of Allowance received from the USPTO dated Jun. 7, 2019 for U.S. Appl. No. 15/908,469, 14 pgs.
Nguyen, Hieu P., Notice of Allowance received from the USPTO dated Jul. 11, 2019 for U.S. Appl. No. 16/025,873, 23 pgs.
pSEMI Corporation, Preliminary Amendment filed in the USPTO dated May 29, 2018 for U.S. Appl. No. 15/908,469, 6 pgs.
pSEMI Corporation, Response filed in the USPTO dated Oct. 30, 2018 for U.S. Appl. No. 15/908,469, 9 pgs.

* cited by examiner

COMPACT HUMIDITY AND PRESSURE SENSOR WITH TEMPERATURE CONTROL

CROSS-REFERENCE TO RELATED APPLICATIONS—CLAIM OF PRIORITY

This application is a continuation of, and claims the benefit of priority under 35 USC § 120 of, commonly assigned and co-pending prior U.S. application Ser. No. 17/195,027, filed Mar. 8, 2021, entitled "Compact Humidity and Pressure Sensor with Temperature Control", the disclosure of which is incorporated herein by reference in its entirety. application Ser. No. 17/195,027 claims priority to U.S. Provisional Application No. 62/987,245 filed on Mar. 9, 2020, the disclosure of which is incorporated herein by reference in its entirety.

BACKGROUND

(1) Technical Field

This invention relates to integrated circuit (IC) electronic circuits and environmental sensors.

(2) Background

Products are known that comprise an application specific integrated circuit (ASIC) die packaged with a separate pressure sensor die and a separate humidity sensor die. Such products may be used, for example, as environment monitors in "smart" cellphones and watches, personal wellness devices, and in automotive applications. The separate sensor dies may be stacked on top of the ASIC die and/or assembled on a circuit board or the like adjacent the ASIC die. The ASIC die and the sensor dies are typically enclosed by a protective shell that includes a vent hole that allows external ambient air to enter inside the shell so as to interact with the pressure and humidity sensors.

A problem with such packaging is that separate dies for both sensors causes increased parasitic capacitance from the sensor dies to the ASIC, which in turn reduces the signal to noise ratio (SNR) of signals provided to the ASIC from the sensor dies. Further, separate sensor dies limit the degree of miniaturization of package for the product as a whole. In addition, the vent hole location may be sub-optimal with respect to both sensor dies.

The present invention addresses these and other problems.

SUMMARY

The invention encompasses novel environmental and temperature sensors in combination with measurement circuitry fully integrated as part of an ASIC die, which may be co-packaged with a pressure sensor IC to create a compact yet sensitive environment monitoring product. The invention also encompasses one or more integrated local heating elements and control circuitry that are power supply independent, make efficient use of battery power, include an accurate in-built temperature detection capability, and provide digital close-loop control of the heating elements.

Embodiments include an integrated circuit die including a surface layer; at least one capacitor structure formed as part of the surface layer, each capacitor structure including a first capacitor terminal, a second capacitor terminal in spaced relationship with respect to the first capacitor terminal, and an environmentally sensitive material formed between, and optionally around, the first and second capacitor terminals as a dielectric, the environmentally sensitive dielectric material being responsive to a selected environmental characteristic so as to cause a measurable change in capacitance and/or electrical charge across the capacitor structure; a capacitance analog-to-digital converter configured to receive an analog signal from at last one capacitor structure indicative of a change in capacitance, $\Delta C$, in the at least one capacitor structure and convert the received analog signal to a corresponding $\Delta C$ digital signal; and a digital signal processor, coupled to the capacitance analog-to-digital converter and configured to generate and output a response based on one or more received $\Delta C$ digital signals.

Some embodiments further include a temperature analog-to-digital converter configured to receive an analog signal from at least one temperature-sensitive sensor indicative of a change in temperature, $\Delta T$, and convert the received analog signal to a corresponding $\Delta T$ digital signal, wherein the digital signal processor is coupled to the temperature analog-to-digital converter and further configured to generate and output a response based on one or more received $\Delta T$ digital signals.

Some embodiments include an integrated circuit heating element and control circuit including a switch device having a control input, a first terminal, and a second terminal configured to be coupled to a supply voltage; a voltage scaling circuit having a scaled voltage output, a first terminal, and a second terminal configured to be coupled to circuit ground; a heating element coupled to the first terminal of the switch device and the first terminal of the voltage scaling circuit; a gain control having a voltage input configured to be coupled to a reference voltage, a digital input configured to be coupled to a source of gain control bits, and an output configured to provide a scaled reference voltage; and an amplifier having a first input coupled to the scaled voltage output of the voltage scaling circuit, a second input the output of the gain control, and an output coupled to the control input of the switch device.

The details of one or more embodiments of the invention are set forth in the accompanying drawings and the description below. Other features, objects, and advantages of the invention will be apparent from the description and drawings, and from the claims.

DETAILED DESCRIPTION

The invention encompasses novel environmental and temperature sensors in combination with measurement circuitry fully integrated as part of an ASIC die, which may be co-packaged with a pressure sensor IC to create a compact yet sensitive environment monitoring product. The invention also encompasses one or more integrated local heating elements that are power supply independent, make efficient use of battery power, include an accurate in-built temperature detection capability, and provide digital close-loop control of the heating elements.

Figure 1:
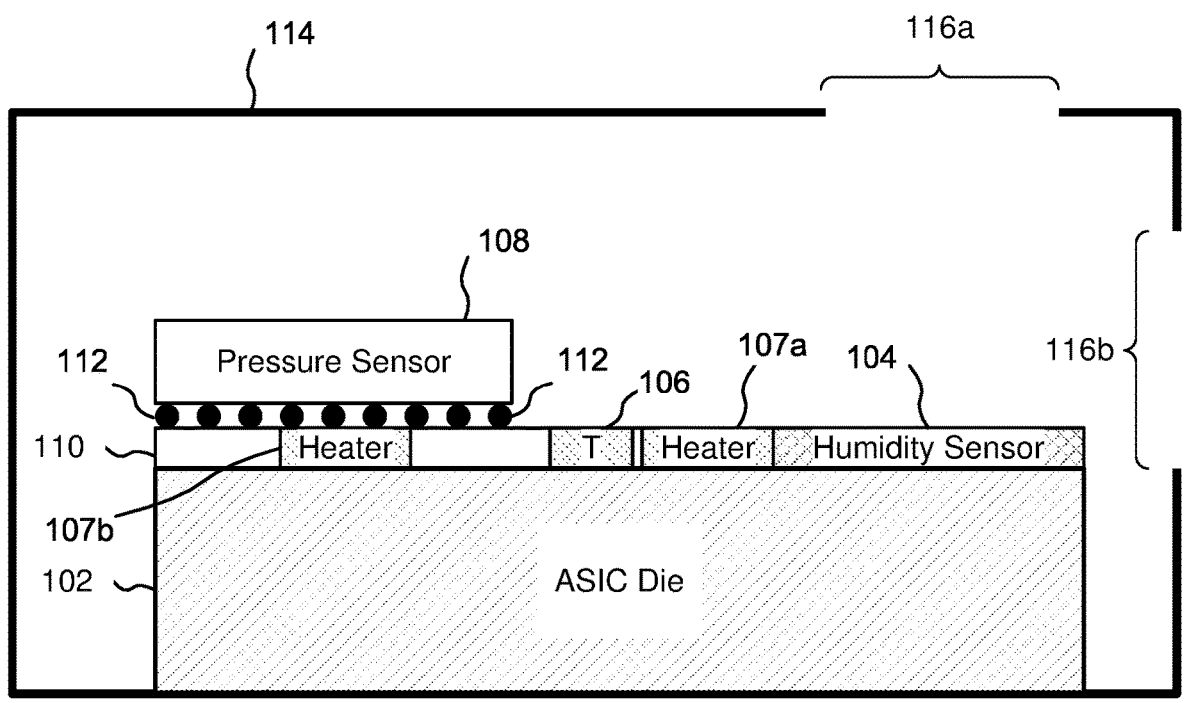
FIG. 1 is a cross-sectional diagram of one embodiment of a product that includes an ASIC die having a fully integrated humidity sensor, optional temperature sensor, and optional heaters in combination with a conventional pressure sensor die.

FIG. 1 is a cross-sectional diagram of one embodiment of a product 100 that includes an ASIC die 102 having a fully integrated humidity sensor 104, an optional temperature sensor 106, and optional heaters 107a, 107b in combination with a conventional pressure sensor die 108. The pressure sensor die 108 is mounted to a surface layer 110 of the ASIC die 102 by conventional means, such as solder ball connections 112. In some embodiments, the pressure sensor die 108 may be mounted on the surface layer 110 so as to overhang the edge of the ASIC die 102, for example, to allow additional area for the humidity sensor 104.

Other embodiments may include different combinations of the integrated humidity sensor 104, the temperature sensor 106, the heaters 107a, 107b, and the pressure sensor die 108. For example, a first alternative embodiment may include only the integrated humidity sensor 104 and a temperature sensor 106, and optionally one or more of the heaters 107a, 107b, while a second alternative embodiment may include the integrated humidity sensor 104, the temperature sensor 106, and a pressure sensor die 108, and optionally one or more of the heaters 107a, 107b.

The ASIC die 102 (including the integrated humidity sensor 104 and the temperature sensor 106 and the heaters 107a, 107b if present) and the mounted pressure sensor die 108 are housed in a protective enclosure 114, which may have one or more openings 116a, 116b that allow external ambient air to enter inside the enclosure 114 so as to interact with the humidity sensor 104 and the temperature sensor 106. Because the humidity sensor 104 is fully integrated with the ASIC die 102, the humidity sensor 104 may be positioned closer to the mounted pressure sensor die 108. Accordingly, it is easier to optimally position the one or more openings 116a, 116b with respect to both the mounted pressure sensor die 108 and the humidity sensor 104 to allow good ambient exposure to both sensors.

As is known in the art, the front-end-of-line (FEOL) is the first portion of IC fabrication where individual active devices (e.g., transistors) and some passive devices (e.g., capacitors, resistors, etc.) are patterned on or in a semiconductor wafer in a primary circuit layer. The FEOL generally covers everything up to (but not including) the deposition of metal interconnect layers. After the last FEOL step, the result is a wafer with isolated transistors (i.e., without any wiring connections). The back-end-of-line (BEOL) is the second portion of IC fabrication where the individual devices are interconnected with conductive wiring or traces on the wafer in a "superstructure" that includes contacts, insulating layers (dielectrics), metal levels, vias, some passive devices (e.g., inductors, capacitors, resistors, etc.), and bonding sites for chip-to-package connections.

Some BEOL fabrication processes include application of a redistribution layer (RDL), which is generally an extra metal layer on an IC die that makes the input/output (I/O) pads of an IC die available to be coupled to other locations of the die, and/or to another IC die, and/or to specialized packing structures. The RDL may be formed on the superstructure, or in some cases (for example, for single-layer transfer chip structures) adjacent to the primary circuit layer after removal of the semiconductor wafer and re-attachment of the primary circuit layer and superstructure to a handle wafer. For purposes of this disclosure, the RDL is considered to be part of the surface layer 110 described above.

Figure 2:
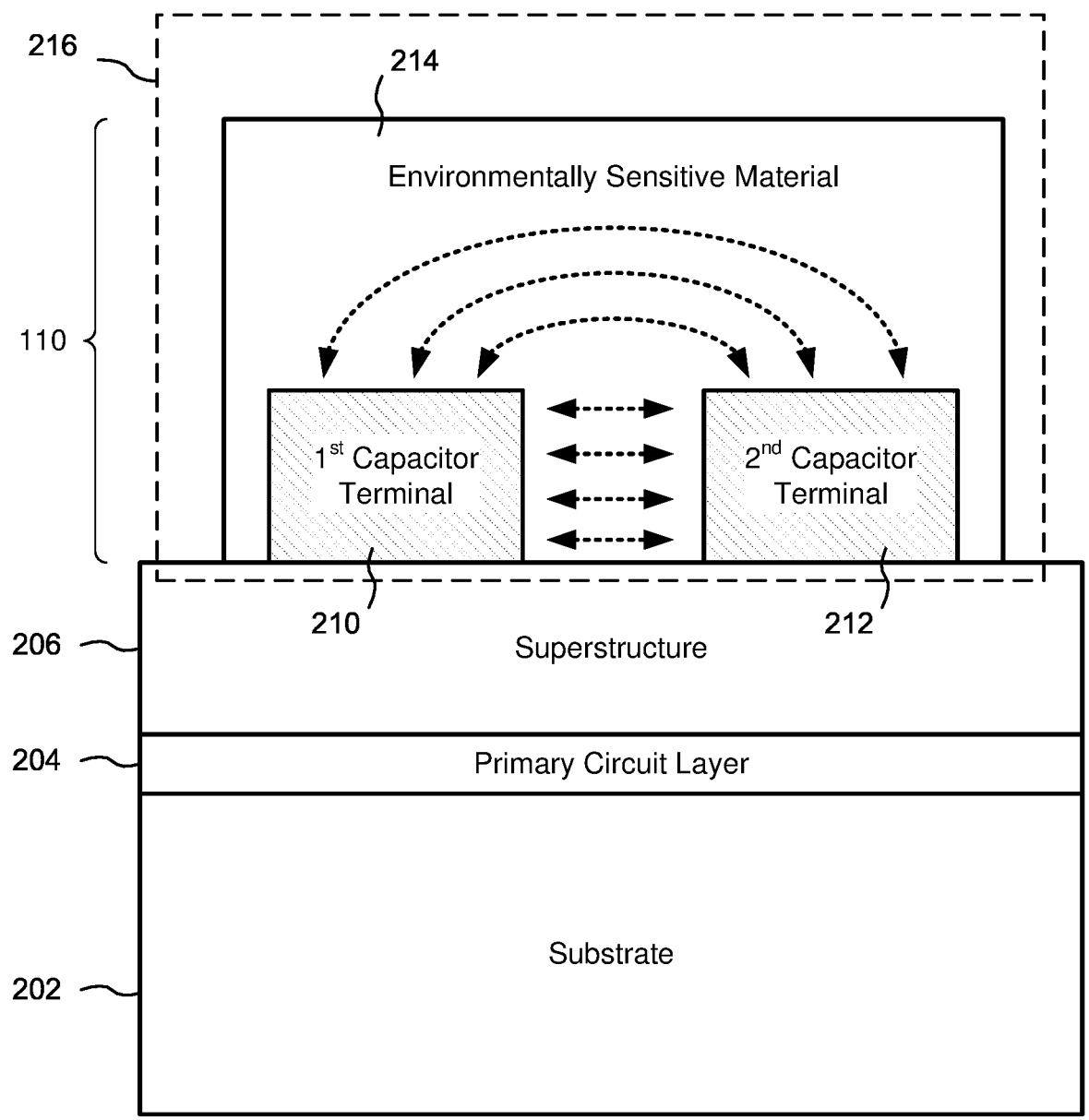
FIG. 2 is a cross-sectional view of an ASIC die having a fully integrated environmental sensor that may be an integrated part of the ASIC die of FIG. 1.

An aspect of the present invention is the formation of one or more fully integrated humidity sensors 104 on an ASIC die 102. For example, FIG. 2 is a cross-sectional view of an ASIC die 200 having a fully integrated environmental sensor that may be an integrated part of the ASIC die 102 of FIG. 1. A substrate 202, such as a silicon or silicon-on-insulator (SOI) wafer, supports a primary circuit layer 204 formed during an FEOL processing stage. A superstructure 206 is formed on the primary circuit layer 204 during a BEOL processing stage. In the illustrated embodiment, the surface layer 110 (see FIG. 1) is formed on the superstructure 206 during the BEOL processing stage. (Note that the dimensions for the various elements in FIG. 2 are not to scale; some dimensions have been greatly exaggerated vertically and/or horizontally for clarity or emphasis.)

A portion of the surface layer 110 includes a first capacitor terminal 210 and a second capacitor terminal 212. Both of the capacitor terminals 210, 212 may be formed of a conductor (e.g., aluminum, copper, conductive polymer, etc.) configured to form two plates of a capacitor. The capacitor terminals 210, 212 may be fabricated out of part of the RDL formed during a BEOL processing stage, and may be configured as two parallel conductor strips, or as a set of interdigitated "comb" like structures, or as concentric circles, etc., in spaced relationship with respect to each other. The dimensions of the capacitor terminals 210, 212, and/or the spacing between the capacitor terminals 210, 212, may be optimally chosen by modeling and/or fabricating test ICs to maximize signal to noise ratio for data conversion circuitry (see below), and/or to optimize key performance parameters of the environmental sensor.

Each of the first capacitor terminal 210 and the second capacitor terminal 212 would generally be coupled to conductive pads or wiring traces on or within the superstructure 206, and thence to circuitry formed in the primary circuit layer 204. An advantage of forming the capacitor terminals 210, 212 as part of the RDL is that, at least for a standard CMOS fabrication process, formation of the capacitor terminals 210, 212 requires no additional masks or process steps, and therefore no additional cost.

One added step would be the deposition and, optionally, shaping, of an environmentally sensitive dielectric material 214 between, and optionally around, the capacitor terminals 210, 212. The deposition and optional shaping of such materials is well known in the art. The first capacitor terminal 210, the environmentally sensitive dielectric material 214, and the second capacitor terminal 212 form a capacitor structure 216 (within the dashed box). Useful capacitance results from parallel plate and fringe capacitance through the environmentally sensitive dielectric material 214. For example, in the illustrated example, applying a voltage across the first capacitor terminal 210 and the second capacitor terminal 212 results in a parallel electric field between the terminals 210, 212 (indicated by the straight dotted lines in FIG. 2) and a fringe electric field between the terminals 210, 212 (indicated by the curved dotted lines in FIG. 2).

For a humidity sensor, the environmentally sensitive dielectric material 214 should, in response to varying environmental moisture levels, cause a measurable change in capacitance and/or electrical charge across the capacitor structure comprising the first capacitor terminal 210, the environmentally sensitive dielectric material 214, and the second capacitor terminal 212. An example of an environmentally sensitive dielectric material 214 responsive to humidity levels is a polymer such as a polyimide, which has a dielectric constant that varies as a function of humidity. As should be appreciated, it is generally preferably to select an environmentally sensitive dielectric material 214 that provides repeatably and easily measured changes in capacitance or charge across the capacitor structure. However, for some products (e.g., one-time low or high threshold monitors for shipped goods), the environmentally sensitive dielectric material 214 does not necessarily have to monitor a range of moisture content, but only need indicate if a threshold "trip" level has been surpassed, and thus need not be repeatable.

In alternative or additional embodiments, the environmentally sensitive dielectric material 214 may cause a measurable change in capacitance and/or charge across the capacitor structure in response to adherence or binding to a target biological or chemical molecule (e.g., carbon monoxide). In other alternative or additional embodiments, materials whose dielectric constants vary as a function of a certain environmental quantity other than the humidity may be used to implement an integrated sensor of that particular quantity.

A single ASIC die 102, 200 may include multiple capacitor structures 216 (i.e., elements 210, 212, 214) within the surface layer 110. The multiple capacitor structures 216 may be all alike (e.g., redundant humidity sensors), or have different environmentally sensitive dielectric materials 214 so as to be responsive to different target environmental quantities or molecules (e.g., a humidity sensor responsive to water within the air, and a chemical sensor responsive to carbon monoxide).

The capacitor structure 216 shown in FIG. 2 has the benefit of requiring no additional masks or process steps to form the capacitor terminals 210, 212, and makes optimal use of standard IC layers to optimize sensing capacitance, and particularly humidity sensing capacitance. Further, fully integrating an environmental sensor comprising the illustrated capacitor structure 216 provides a significant reduction in parasitic capacitance from the capacitor structure 216 to signal processing circuitry within the ASIC die 200, which in turn increases the signal to noise ratio (SNR) of signals provided to the ASIC signal processing circuitry.

Figure 3:
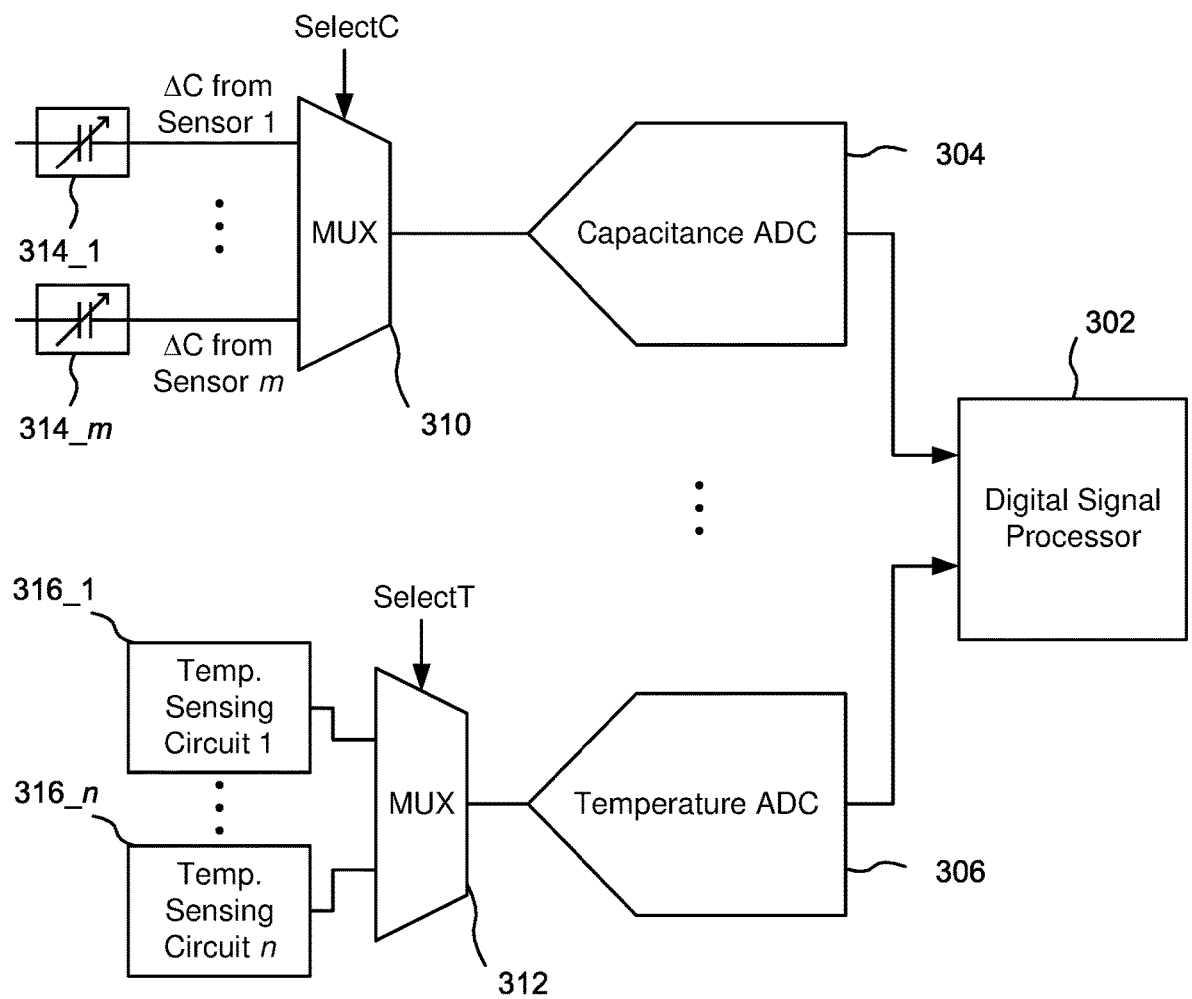
FIG. 3 is a block diagram of one embodiment of a multiplexor circuit that may be fabricated as part of an ASIC die.

Another advantage of fully integrating one or more environmental sensors within an ASIC die 102, 200 is that various sensor inputs (e.g., on-die humidity, off-die pressure) can be multiplexed into the same data converter and processed by the same digital signal processor, providing a significant reduction of ASIC area. For example, FIG. 3 is a block diagram of one embodiment of a multiplexor circuit that may be fabricated as part of an ASIC die 102, 200. A digital signal processor 302, which generally would be part of the signal processing circuitry within the ASIC die 102, 200, is configured to receive inputs from at least one capacitance analog-to-digital converter (ADC) 304, and optionally from other ADC's, such as a temperature ADC 306, and generate and output a response based on the received inputs. The generated response may be, for example, a value that can be mapped to a displayable value (e.g., a humidity or pressure reading) or a value that can be used to control other on-chip circuitry or off-chip circuits or elements, in known fashion.

Each ADC 304, 306 is configured to convert an analog input to a digital signal, in known fashion. The capacitance ADC 304 would be configured and calibrated to receive an analog signal from a capacitor-based circuit indicative of a change in capacitance, $\Delta C$, and convert the received analog signal to a corresponding $\Delta C$ digital signal. Similarly, the temperature ADC 306 would be configured and calibrated to receive an analog signal from a temperature-sensitive circuit indicative of a change in temperature, $\Delta T$, and convert the received analog signal to a corresponding $\Delta T$ digital signal. The analog $\Delta T$ signal may be from an on-die temperature sensor and/or an off-die temperature sensor. Different signal ranges of the input signals to the ADC's 304, 306 can be accounted for in the dynamic range of the ADC's 304, 306, and/or appropriate gain partitioning in the system, and/or by scaling the inputs as needed (e.g., with a voltage divider circuit and/or amplifier circuit, in known fashion).

If more than one signal needs conversion, then one or more multiplexors 310, 312 may be used before the input terminal of a particular ADC 304, 306, allowing output signals from one of a plurality of analog circuits to be selectively coupled to a corresponding ADC 304, 306 under the control of a corresponding selection signal. For example, in the illustrated embodiment, which input to the multiplexor 310 is passed through as an output of the multiplexor 310 is controlled by a SelectC signal; similarly, which input to the multiplexor 312 is passed through as an output of the multiplexor 312 is controlled by a SelectT signal. The selection signals SelectC, SelectT may be generated by the signal processing circuitry within the ASIC die 102, 200, and may be, for example, simple "round-robin" signals that cycle through the possible inputs in a desired order. In other cases, the selection signals SelectC, SelectT may be generated in response to some criteria internal to the signal processing circuitry within the ASIC die 102, 200 and/or some external input (e.g., a button press by a user).

In the example embodiment shown in FIG. 3, a first multiplexor 310 is coupled between the capacitance ADC 304 and $\Delta C$ output signals from a plurality of capacitor-based sensors 314_1 . . . 314_m (collectively, 314_x). One or more of the capacitor-based sensors 314_x may be, for example, like the capacitor structure 216 shown in FIG. 2 and fully integrated with the ASIC die 102, 200. One or more of the capacitor-based sensors 314_x also may be external to the ASIC die 102, 200, such as the pressure sensor die 108 shown in FIG. 1 (as is known, common IC pressure sensors may be based on capacitive structures and circuits).

The illustrated architecture allows combinations of sensors on the same die that not only enhance the functionality of other sensors that require exposure to environment, but can be used for independent sensing. For example, as shown in FIG. 3, a second multiplexor 312 is coupled between the temperature ADC 306 and $\Delta T$ output signals from a plurality of temperature-sensitive sensors 316_1 . . . 316_n (collectively, 316_x). One or more of the temperature-sensitive sensors 316_x may be fully integrated with the ASIC die 102, 200. One or more of the temperature-sensitive sensors 316_x also may be external to the ASIC die 102, 200, such as from a power management integrated circuit (PMIC, not shown) coupled to the ASIC die 102, 200.

In other additional embodiments of the invention, measurable changes in electrical properties other than dielectric constant or capacitance (for example, changes in conductance in response to environmental variables) may be measured to implement different or additional sensors. The BEOL structures may be used in forming passive electrical devices or structures other than capacitors. For example, a conductive polymer whose conductance varies with the presence and amounts of certain gases in the environment may be used in connection with conductive terminals to measure changes in the conductance of the polymer as a basis for sensing presence or amounts of certain gases in the environment.

Figure 4:
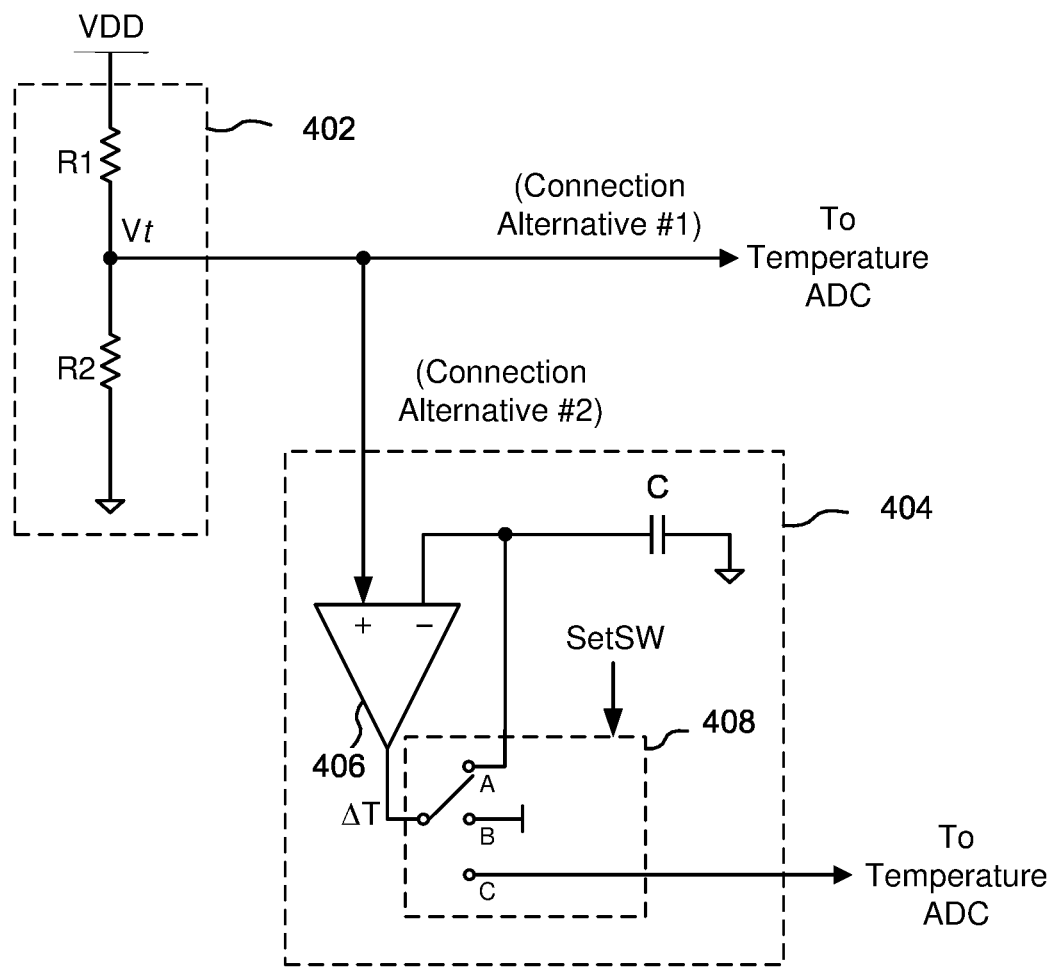
FIG. 4 is a schematic diagram of one embodiment of an analog temperature sensor circuit that may be used as one of the temperature-sensitive sensors in FIG. 3.

FIG. 4 is a schematic diagram of one embodiment of an analog temperature sensor circuit 400 that may be used as one of the temperature-sensitive sensors 316_x in FIG. 3. The temperature sensor circuit 400 includes a temperature-sensitive subcircuit 402 comprising two series-coupled resistors R1, R2 coupled between a voltage supply $V_{DD}$ and circuit ground. The values of one or both of the resistors R1, R2 may be adjustable or settable (e.g., by laser trimming during manufacture) or variable (e.g., by a programmed control signal from the signal processing circuitry within the ASIC die 102, 200). If the resistors R1, R2 are fabricated in reasonably close proximity to another circuit element (e.g., a local heater element, as described below), the node between the resistors R1, R2 will have a voltage $V_t$ that varies as a function of the temperature of the nearby circuit element. As should be clear, a different temperature subcircuit could be used in place of the illustrated resistor-based temperature-sensitive subcircuit 402, such as a diode-based temperature-sensitive subcircuit or subcircuit comprising a negative-temperature-coefficient (NTC) thermistor series-coupled to a resistor. In some embodiments, the voltage $V_t$ output by the temperature-sensitive subcircuit 402 may be coupled to the temperature ADC 306 of FIG. 3, either directly (if there is only one temperature sensor circuit 400) or through the second multiplexor 312.

In other embodiments, the voltage $V_t$ output by the temperature-sensitive subcircuit 402 may be first coupled to a sample-and-hold (S&H) circuit 404. In the example circuit illustrated in FIG. 4, the voltage $V_t$ is coupled to a first input of a differential amplifier 406 which may be, for example, a differential transconductance amplifier (however, other circuits may be used that can generate an output that is a function of the difference between two provided inputs). The output of the differential amplifier 406 is coupled to a 3-terminal switch 408 that may be implemented with field effect transistors (FETs). Terminal A of the switch 408 is coupled to a charge storage capacitor C and to a second input of the differential amplifier 406. Terminal B is an open circuit, and terminal C may be coupled to the temperature ADC 306 of FIG. 3, either directly (if there is only one temperature sensor circuit 400) or through the second multiplexor 312. The state of the switch 408 may be set by a timing control signal SetSW from signal processing circuitry within the ASIC die 102, 200.

In operation, during a sampling interval, the timing control signal SetSW sets the switch 408 of the S&H circuit 404 to couple the output of the differential amplifier 406 to terminal A as an initial sampling state. As a consequence, the capacitor C will be charged up until both inputs to the differential amplifier 406 are equal to $V_t$, the voltage representing the momentary temperature of a circuit element being monitored (i.e., nearby the temperature-sensitive subcircuit 402). More precisely, for the case where the differential amplifier 406 is a transconductance amplifier, the voltage on the positive input will be $V_t$, but the voltage on the negative input (and on the capacitor C) will be the combination of $V_t$ and the inverse of the cumulative offsets (imbalances) in the differential amplifier 406 required to set its output current to zero (once the voltage on the capacitor C settles to a static value, no current can flow). Accordingly, the S&H circuit 404 in effect calibrates out all of its offsets during the sampling phase, and the capacitor C is in essence constantly tracking the temperature of the circuit element being monitored.

After a short delay (e.g., about 5-10 μS), the timing control signal SetSW sets the switch 408 of the S&H circuit 404 to couple the output of the differential amplifier 406 to terminal B, and thus uncouple the capacitor C from any further input from the differential amplifier 406; the transition to terminal B provides a non-overlapping switching sequence to reduce sampling errors. At the time $t=t_0$ that the timing control signal SetSW activates terminal B, the capacitor C holds a charge that represents the temperature $T(t=t_0)$ of the circuit element being monitored (as well as any associated S&H circuit 404 offsets, so as to effectively dynamically calibrate out such offsets as noted above). Thus, coupling the output of the differential amplifier 406 to terminal B for a brief (e.g., 0.1-1 μS) transition period allows the circuitry to settle to a new state, thereby avoiding transients in other circuitry while holding a sampled charge on the capacitor C.

Thereafter, the timing control signal SetSW sets the switch 408 to couple the output of the differential amplifier 406 to terminal C for a time $t>t_0$ (i.e., the time after $t_0$). When the S&H circuit 404 is in this configuration, one input of the differential amplifier 406 is the stored charge (voltage) on the capacitor C, representing the temperature $T(t=t_0)$, while the other input of the differential amplifier 406 is $V_t$, representing the temperature $T(t>t_0)$—that is, the continuously measured temperature of the circuit element being monitored. The output of the differential amplifier 406 is ΔT, which represents the difference between the initial temperature $T(t=t_0)$ and the subsequently measured temperature $T(t>t_0)$ of the circuit element being monitored. As should be clear, other sample and hold circuits may be used to determine $\Delta T = T(t>t_0) - T(t=t_0)$ for the circuit element being monitored.

Referring back to FIG. 1, the resistors R1, R2 temperature-sensitive subcircuit 402 of FIG. 4 may be formed in the RDL of the surface layer 110, since the conductive material of the RDL may be used to form resistive elements. As should be clear, one or more temperature-sensitive subcircuit 402 may be formed in the surface layer 110 so that temperature measurements can be made at one or more locations. For example, it may be useful to measure different portions of the ASIC die 102, 200 for local heating issues. Further, as described below, it may be useful to monitor the actual temperature of one or more of the heaters 107a, 107b to provide a closed feedback loop for control purposes.

Accordingly, as set out in detail above, using the first multiplexor 310, multiple capacitor-based sensors 314_x can be interfaced to the same capacitance ADC 304 within the signal processing circuitry of an ASIC die 102, 200, and similarly, using the second multiplexor 312, multiple temperature-sensitive sensors 316_x can be interfaced to the same temperature ADC 306 within the signal processing circuitry of an ASIC die 102, 200.

In some embodiments, it is useful to be able to generate a controlled temperature for at least part of an IC die for such purposes as field re-calibration of sensors due to temperature dependence and/or evaporation of water after a condensation event. For example, a pressure sensor may have a pressure measurement dependence on temperature that is initially factory calibrated. With a controlled temperature rise using a local-area heater on or near the pressure sensor, the remnant error in factory calibration could be further reduced in the field. In addition, due to aging and other factors, an initial factory temperature-dependent calibration might become less effective in the field, thus making occasional temperature-controlled recalibration desirable. As another example, a local-area heater on or near a humidity sensor and/or a pressure sensor could be used to increase temperature beyond the dew point, enabling condensed water to evaporate and allowing the sensor to resume normal functioning. As should be appreciated by those of ordinary skill in the art, an ability to heat at least part of an IC die may be useful for other types of sensors and for non-sensor purposes.

Figure 5A:
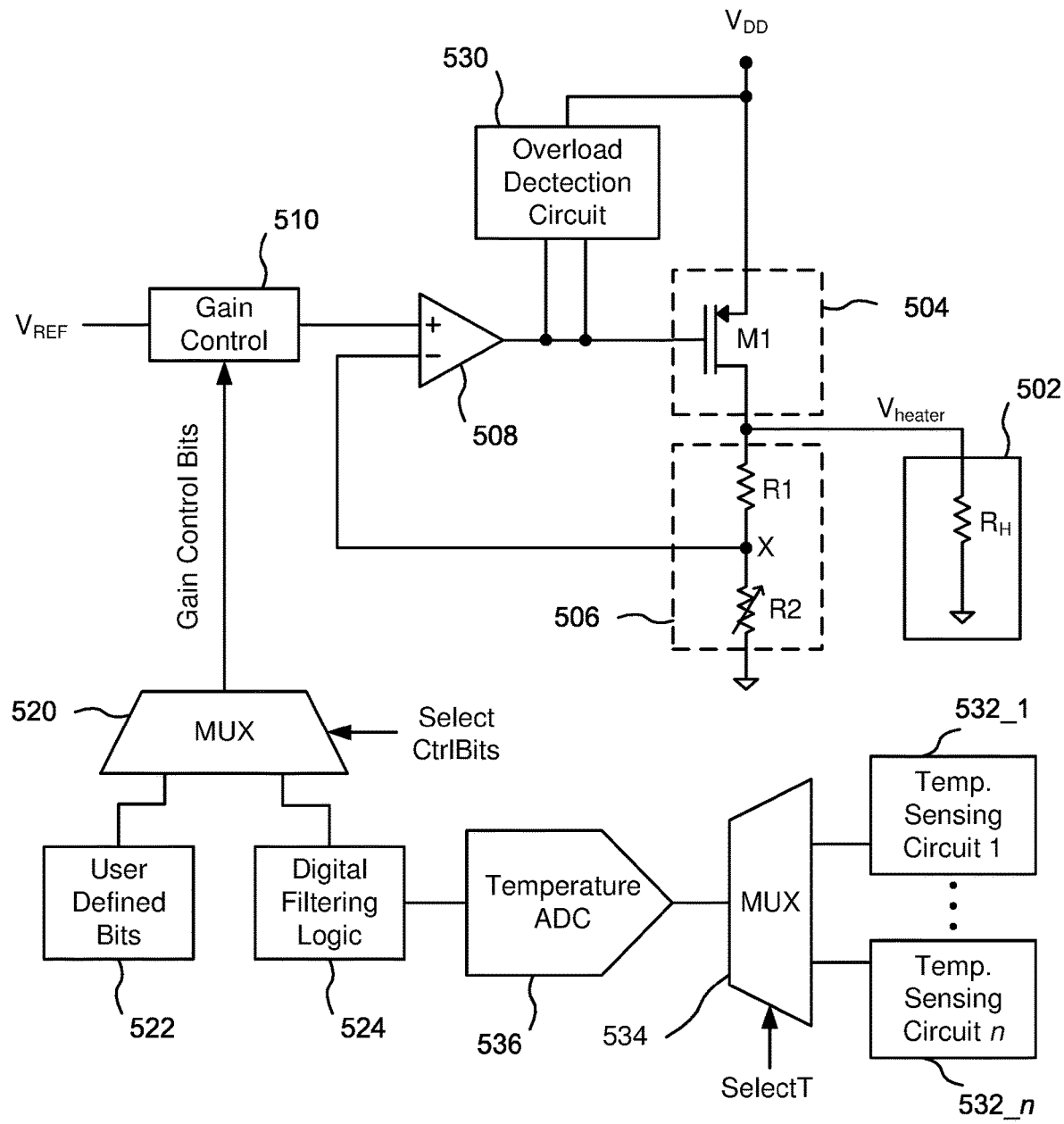
FIG. 5A is a block diagram of one embodiment of an integrated circuit heating element and control circuit.

FIG. 5A is a block diagram of one embodiment of an integrated circuit heating element and control circuit 500. The heating element and control circuit 500 may be fabricated as part of an ASIC die 102, 200. In the illustrated example, a heating element 502 (which may comprise, for example, a resistor $R_H$) is coupled to a first terminal of a switch device 504 (shown as a PMOS field effect transistor M1) and a first terminal of a voltage scaling circuit 506. A second terminal of the switch device 504 is configured to be coupled to a supply voltage $V_{DD}$. A second terminal of the voltage scaling circuit 506 is configured to be coupled to circuit ground.

An embodiment may include one or more heating elements 502. For example, the heating elements 502 may be used for the heaters 107a, 107b shown in FIG. 1. For some embodiments, the heating element 502 would be positioned in parts of an ASIC die 102, 200 that would benefit from localized heating, such as within the surface layer 110 of the ASIC die 102, 200 near the integrated humidity sensor 104, as shown in FIG. 1 by way of example (see heater 107a). For some embodiments, the heating element 502 would be positioned within the surface layer 110 of the ASIC die 102, 200 near or underneath an external die, such as the pressure sensor die 108 shown in FIG. 1 (see heater 107b).

In the example shown in FIG. 5A, the voltage scaling circuit 506 is a resistive divider comprising series-coupled resistors R1, R2 coupled between the switch device 504 and circuit ground. The values of one or both of the resistors R1, R2 may be adjustable or settable (e.g., by laser trimming during manufacture) or variable (e.g., by a programmed control signal from the signal processing circuitry within the ASIC die 102, 200). A scaled voltage output of the voltage scaling circuit 506 is also coupled to a first input of an amplifier 508, which may be, for example, a differential amplifier. In the illustrated example, the scaled voltage output of the voltage scaling circuit 506 is a node X between the series-coupled resistors R1, R2. The ratio of the resistors R1, R2 will determine the amount of the voltage coming through the switch device 504 that will be applied to the first input of the amplifier 508.

A second input of the amplifier 508 is coupled to a conventional gain control circuit 510, which is in turn coupled to a reference voltage $V_{REF}$. The reference voltage $V_{REF}$ preferably provides a well-regulated, temperature-independent voltage. For example, the reference voltage $V_{REF}$ may be generated by a conventional bandgap voltage reference circuit (not shown). Applied Gain Control Bits generally would be converted within the gain control circuit 510 to an analog value (e.g., by means of an internal A-to-D converter circuit) and that value would be compared to $V_{REF}$ to provide a control signal to the amplifier 508.

The gain control circuit 510 can provide fine control of the voltage applied to the second input of the amplifier 508 under the control of the applied Gain Control Bits. As an example, four Gain Control Bits would allow any of 16 voltage levels to be selected, while eight Gain Control Bits would allow any of 256 voltage levels to be selected. In general, one value for the Gain Control Bits should cause the amplifier 508 to turn the switch device 504 OFF, so that no appreciable current flows through the heating element 502. In the illustrated example, the Gain Control Bits provided to the gain control circuit 510 may be selected by a multiplexor 520 from external, user supplied control bits 522, or from a digital filter logic circuit 524 (see further description below). A SelectCtrlBits signal, which may be from signal processing circuitry within the ASIC die 102, 200, controls which input to the multiplexor 520 is passed through as an output of the multiplexor 520 to the gain control circuit 510. In some implementations, in order to achieve still finer resolution control, gain control may be performed by varying the duty cycle of the control bits in addition to setting various values for the bits themselves. For example, it may be that a setting of "3" for the Gain Control Bits does not provide sufficient heat through the heating element 502, while a setting of "4" for the Gain Control Bits provides too much heat through the heating element 502. Accordingly, the Gain Control Bits may be set to "4" to provide a relatively high level of heat, and then cycled to another value (e.g., "0" or OFF, or another level, such as "3") to provide no heat or a lower level of heat, such that the average heat generated by the heating element 502 is at a desired level. Accordingly, intermediate heating levels can be selected for the heating element that have a finer resolution than the steps provided by the Gain Control Bits. In other embodiments, the reference voltage $V_{REF}$ to the gain control circuit 510 may be varied to provide intermediate heating levels for the heating element.

The output of the amplifier 508 is coupled to a control input of the switch device 504 (e.g., the gate of transistor M1). The output of the amplifier 508 controls current flow through the switch device 504 as a function of the difference between a feedback voltage generated by the voltage scaling circuit 506 (e.g., the voltage at node X) and $V_{REF}$, as selectively scaled by the gain control circuit 510. Accordingly, the amplifier 508 regulates the current through any coupled heating elements 502 by forcing a voltage $V_{heater}$ across the heating element 502 through a feedback loop.

When more than one heating element 502 is used, it may be beneficial to insert a multiplexor (not shown) between the switch device 504 and the plurality of heating elements 502 so that only one heating element 502 is coupled to the switch device 504 at a time. Alternatively, the control circuitry shown in FIG. 5A for the single illustrated heating element 502 may be replicated for each additional heating element 502.

Figure 6:
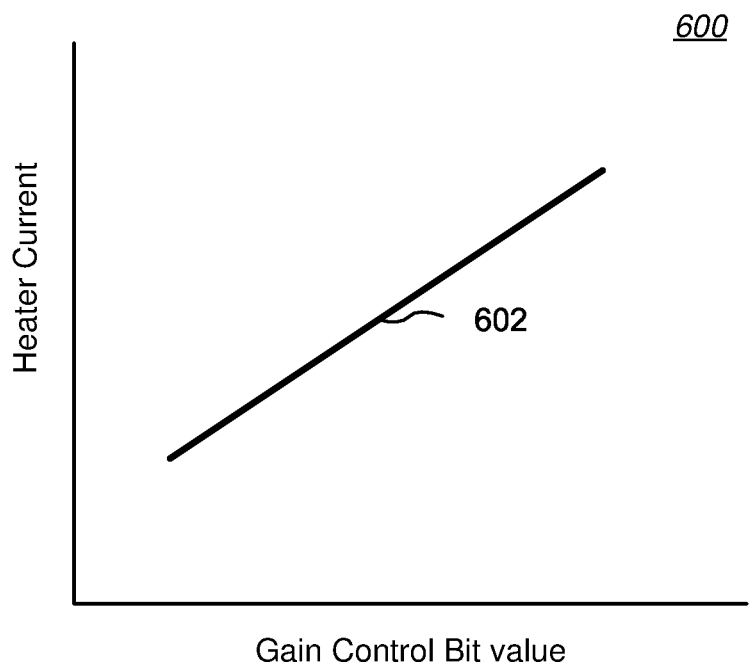
FIG. 6 is a graph showing that the heater current allowed through the switch device to the heating element varies linearly with the Gain Control Bit value.
Figure 7:
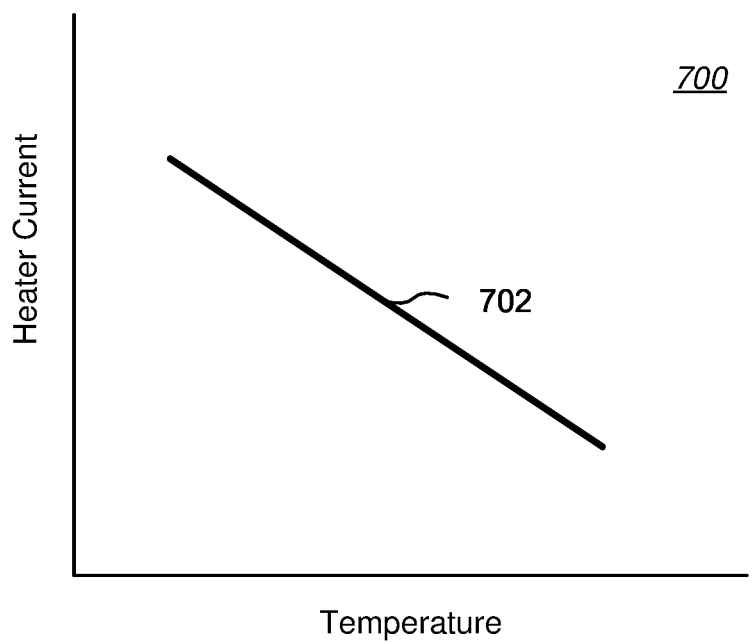
FIG. 7 is a graph showing that the heater current through the heating element varies inversely with respect to temperature Like reference numbers and designations in the various drawings indicate like elements.

The heating element and control circuit 500 of FIG. 5A provides a high correlation between Gain Control Bit value and temperature. For example, FIG. 6 is a graph 600 showing that the heater current allowed through the switch device 504 to the heating element 502 varies linearly with the Gain Control Bit value. Thus, the higher the Gain Control Bit value, the more current is allowed through the switch device 504 to the heating element 502, as indicated by graph line 602 (the exact bit values and current values are not important, and thus not shown). In contrast, FIG. 7 is a graph 700 showing that the heater current through the heating element 502 varies inversely with respect to temperature. Thus, the higher the Gain Control Bit value, the more current is allowed through the switch device 504 to the heating element 502, which means that the temperature of the heating element 502 is reduced, as indicated by graph line 702 (again, the exact current and temperature values are not important, and thus not shown). For example, the resistance of aluminum, a common IC conductive material, increases with temperature. The two relationships shown in FIGS. 6 and 7 enable, in combination, calculation of the particular Gain Control Bit value needed for a desired temperature value.

Another aspect of the heating element and control circuit 500 of FIG. 5A is the inclusion of a fast analog overload detection circuit 530 coupled to the output of the amplifier 508 and to the control input of the switch device 504. The overload detection circuit 530 disables current flow to the heating element 502 in the event of a high current fault through the heating element 502.

Figure 5B:
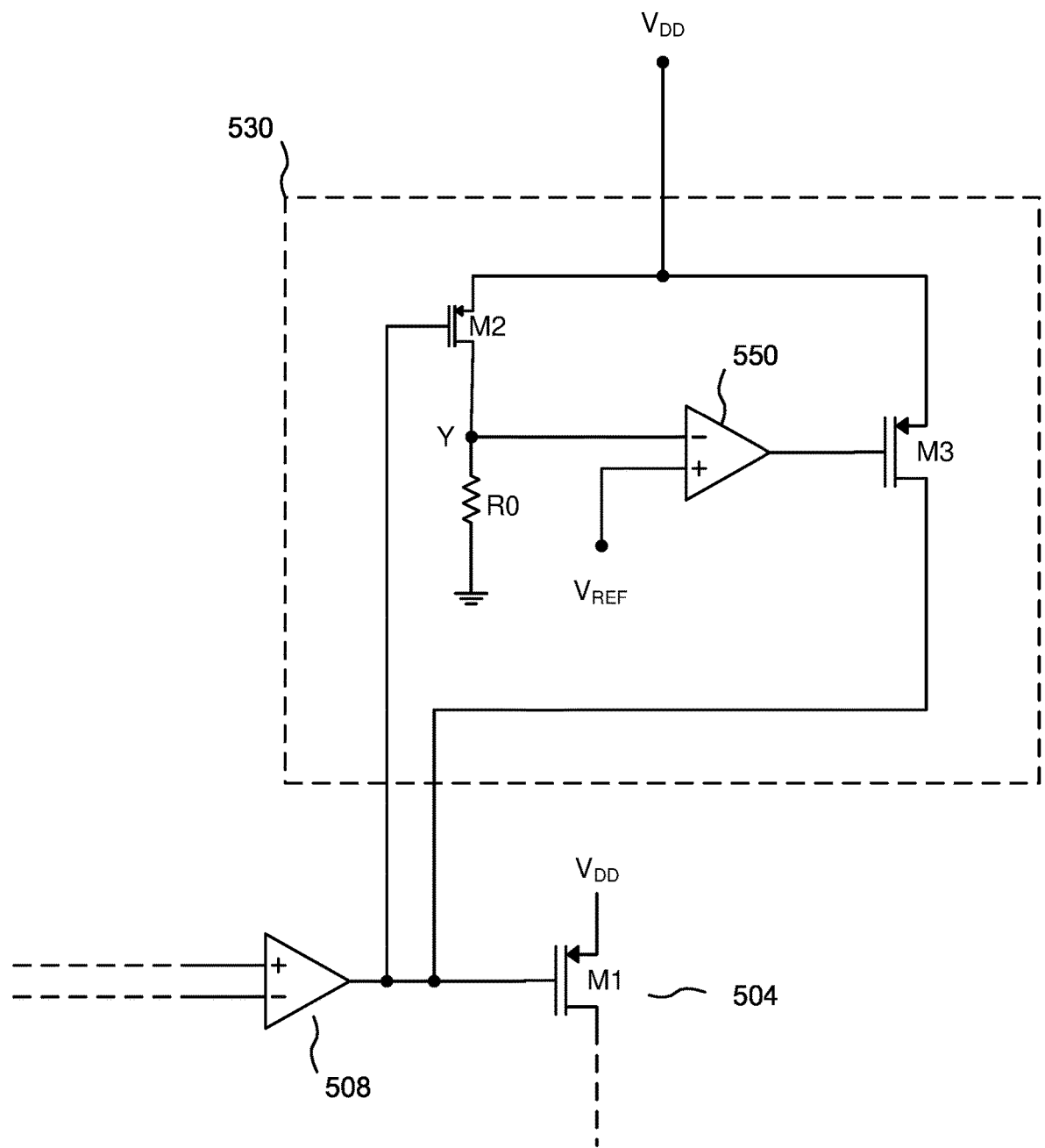
FIG. 5B is a schematic diagram of one embodiment of the overload detection circuit of FIG. 5A.

FIG. 5B is a schematic diagram of one embodiment of the overload detection circuit 530 of FIG. 5A. In the illustrated example, the overload detection circuit 530 includes a "mirror" of the switch device 504, implemented as a reduced-scale PMOS FET M2. The gate of the PMOS FET M2 is coupled to the output of the amplifier 508. FET M2 is coupled between a supply voltage $V_{DD}$ and a resistor R0, which in turn is coupled to circuit ground. As is known in the art, a mirror current through FET M2 and the resistor R0 will generate a voltage at node Y. The generated voltage from FET M2 is compared against a reference voltage $V_{REF}$ in a comparator 550. A difference between the generated voltage from FET M2 and $V_{REF}$ due to an excessive amount of current being mirrored through FET M2 will cause the output of the comparator 550 to change (in the illustrated circuit, by going from HIGH to LOW). The output of the comparator 550 is coupled to a switch (shown here as PMOS FET M3), which couples $V_{DD}$ to the gate of FET M1 when triggered by the state change of the output of the comparator 550, thus disabling the switch device 504. The overload detection circuit 530 thus prevents supply voltage dips in $V_{DD}$, or "brown outs", due to excessive current draw by the heating element 502. This is important since a number of other circuits are generally dependent on the stability of the $V_{DD}$ supply voltage. As should be appreciated, a number of other circuits may be used to accomplish the function of the overload detection circuit 530.

Yet another aspect of the heating element and control circuit 500 of FIG. 5A is the inclusion a digital closed loop control circuit to achieve a desired temperature rise. For example, in FIG. 5A, one or more temperature-sensitive sensors 532_1 . . . 532_n (collectively, 532_x) are coupled through an optional multiplexor 534 (only needed if more than one temperature-sensitive sensor 532_x is used) to a temperature ADC 536. The output of the temperature ADC 536 is coupled to the digital filter logic circuit 524 mentioned above. The digital filter logic circuit 524 may provide a number of filtering functions such as averaging a set of temperature signals from one or more of the temperature-sensitive sensors 532_x and/or omitting values that are deemed to be spurious (e.g., extremely high or low temperature readings that may be due to electronic noise). The digital filter logic circuit 524 may also apply a mapping function that maps digital temperature values from the temperature ADC 536 to a Gain Control Bits. Through a calibration process, which may include circuit modeling and/or actual testing of IC dies, a determination can be made of the Gain Control Bit values needed to achieve a desired temperature rise for a local region near a heater element 502.

One or more of the temperature-sensitive sensors 532_x may be fully integrated with an ASIC die 102, 200, as described above with respect to FIGS. 3 and 4. One or more of the temperature-sensitive sensors 532_x may be external to the ASIC die 102, 200. For example, an external temperature-sensitive sensor 532_x may be thermally coupled to or within another integrated circuit, such as a power management integrated circuit (PMIC, not shown) coupled to the ASIC die 102, 200. Such external temperature-sensitive sensors 532_x may provide temperature readings for critical regions of another circuit element within a product, allowing the heating element and control circuit 500 of FIG. 5A to determine whether to allow current flow through a heater element 502. For example, a high external temperature reading may indicate that high currents are being drawn by another circuit element within a product (e.g., a pressure sensor 108 mounted on an ASIC die 102). Since the product often has only one power source at a time (e.g., just a battery), current flow through a heater element 502 may be turned OFF under such circumstances to conserve battery power. For off-die temperature-sensitive sensors 532_x, it may be useful to locally (i.e., near the temperature-sensitive sensor 532_x) convert the analog temperature values to digital form and couple the digital signals directly to the digital filter logic circuit 524. Doing so avoids propagation degradation of the analog output of the off-die temperature-sensitive sensors 532_x.

The heating element and control circuit 500 of FIG. 5A provides several advantages:
  a. The ability to include one or more heating elements 502 as part of an ASIC die 102, 200 enables localized increases in die temperature in a controlled manner.
  b. The single switch device 504 allows the voltage across a heating element 502, $V_{heater}$, to be very close in value to $V_{DD}$, thus dissipating a majority of the supply voltage across the heating element 502 and thereby efficiently using the supply voltage to generate heat. Since $V_{DD}$ may be supplied by a battery, efficient energy usage is important in many applications.
  c. The temperature and supply independent reference voltage $V_{REF}$ enables the $V_{heater}$ voltage across a heating element 502 to be independent of $V_{DD}$ (often supplied from a battery, which may not output a constant voltage), as well as be independent from internal and external temperatures.
  d. The Gain Control Bits allow fine control over the voltage—and thus current—across a heating element 502, and thus allows fine control of the temperature.
  e. Gain Control Bits can be controlled by a user or by a digital closed loop control which feeds back detected temperature information.
  f A built-in fault detection circuit prevents supply voltage dips ("brown outs") due to excessive heater current draw.
  g. An on-die temperature sensing circuit allows a more accurate estimate of local temperature than an off-die temperature sensing circuit.

Another aspect of the invention includes methods for integrating novel environmental and temperature sensors in combination with measurement and processing circuitry fully integrated as part of an ASIC die, including co-packaging the ASIC die with a pressure sensor IC, for example, to create a compact yet sensitive environment monitoring product. The methods include providing the components and circuit elements described above, and/or performing the functions of such components and circuit elements.

In some applications, a temperature and/or a fully integrated capacitive sensor implemented according to the embodiments of the invention may be integrated and/or fused together with one or more other environmental sensors, such as sensors for sensing one or more gases and/or one or more vapors (e.g., volatile organic compounds or VOCs). The additional environmental sensors may utilize sensor technologies and sensing principles that vary according to the specific gases of interest, such as non-dispersive infrared (NDIR) spectroscopic sensors and carbon nanotube (CNT) sensors. The additional sensor(s) may be integrated on the same ASIC die 102 with a fully integrated capacitive sensor (such as humidity sensor 104), or may be combined in a common circuit structure (such as an IC package or module) with and coupled to an ASIC die 102 having a fully integrated capacitive sensor. Alternatively, the additional sensor(s) may be entirely separate from an ASIC die 102 having a fully integrated capacitive sensor, and the outputs of the additional sensor(s) and the integrated capacitive sensor may be combined or "fused" (for example, using software) to provide information indicative of the presence and/or levels of a variety of gases and/or vapors.

The term "MOSFET", as used in this disclosure, includes any field effect transistor (FET) having an insulated gate whose voltage determines the conductivity of the transistor, and encompasses insulated gates having a metal or metal-like, insulator, and/or semiconductor structure. The terms "metal" or "metal-like" include at least one electrically conductive material (such as aluminum, copper, or other metal, or highly doped polysilicon, graphene, or other electrical conductor), "insulator" includes at least one insulating material (such as silicon oxide or other dielectric material), and "semiconductor" includes at least one semiconductor material.

With respect to the figures referenced in this disclosure, the dimensions for the various elements are not to scale; some dimensions have been greatly exaggerated vertically and/or horizontally for clarity or emphasis. In addition, references to orientations and directions (e.g., "top", "bottom", "above", "below", "lateral", "vertical", "horizontal", etc.) are relative to the example drawings, and not necessarily absolute orientations or directions.

Various embodiments of the invention can be implemented to meet a wide variety of specifications. Unless otherwise noted above, selection of suitable component values is a matter of design choice. Various embodiments of the invention may be implemented in any suitable integrated circuit (IC) technology (including but not limited to MOSFET structures), or in hybrid or discrete circuit forms. Integrated circuit embodiments may be fabricated using any suitable substrates and processes, including but not limited to standard bulk silicon, silicon-on-insulator (SOI), and silicon-on-sapphire (SOS). Unless otherwise noted above, embodiments of the invention may be implemented in other transistor technologies such as bipolar, BiCMOS, LDMOS, BCD, BCDLite, GaAs HBT, GaN HEMT, GaAs pHEMT, and MESFET technologies. However, embodiments of the invention are particularly useful when fabricated using an SOI or SOS based process, or when fabricated with processes having similar characteristics. Fabrication in CMOS using SOI or SOS processes enables circuits with low power consumption, the ability to withstand high power signals during operation due to FET stacking, good linearity, and high frequency operation (i.e., radio frequencies up to and exceeding 50 GHz). Monolithic IC implementation is particularly useful since parasitic capacitances generally can be kept low (or at a minimum, kept uniform across all units, permitting them to be compensated) by careful design.

Voltage levels may be adjusted, and/or voltage and/or logic signal polarities reversed, depending on a particular specification and/or implementing technology (e.g., NMOS, PMOS, or CMOS, and enhancement mode or depletion mode transistor devices). Component voltage, current, and power handling capabilities may be adapted as needed, for example, by adjusting device sizes, serially "stacking" components (particularly FETs) to withstand greater voltages, and/or using multiple components in parallel to handle greater currents. Additional circuit components may be added to enhance the capabilities of the disclosed circuits and/or to provide additional functionality without significantly altering the functionality of the disclosed circuits.

Circuits and devices in accordance with the present invention may be used alone or in combination with other components, circuits, and devices. Embodiments of the present invention may be fabricated as integrated circuits (ICs), which may be encased in IC packages and/or in modules for ease of handling, manufacture, and/or improved performance. In particular, IC embodiments of this invention are often used in modules in which one or more of such ICs are combined with other circuit blocks (e.g., filters, amplifiers, passive components, and possibly additional ICs) into one package. The ICs and/or modules are then typically combined with other components, often on a printed circuit board, to form an end product such as a cellular telephone, laptop computer, or electronic tablet, or to form a higher level module which may be used in a wide variety of products, such as vehicles, test equipment, medical devices, etc. Through various configurations of modules and assemblies, such ICs typically enable a mode of communication, often wireless communication.

A number of embodiments of the invention have been described. It is to be understood that various modifications may be made without departing from the spirit and scope of the invention. For example, some of the steps described above may be order independent, and thus can be performed in an order different from that described. Further, some of the steps described above may be optional. Various activities described with respect to the methods identified above can be executed in repetitive, serial, and/or parallel fashion.

It is to be understood that the foregoing description is intended to illustrate and not to limit the scope of the invention, which is defined by the scope of the following claims, and that other embodiments are within the scope of the claims. In particular, the scope of the invention includes any and all feasible combinations of one or more of the processes, machines, manufactures, or compositions of matter set forth in the claims below. (Note that the parenthetical labels for claim elements are for ease of referring to such elements, and do not in themselves indicate a particular required ordering or enumeration of elements; further, such labels may be reused in dependent claims as references to additional elements without being regarded as starting a conflicting labeling sequence).

What is claimed is:
1. An integrated circuit die including:
(a) at least one sensor structure formed as part of the integrated circuit die and responsive to a selected environmental characteristic so as to cause a measurable change in electrical capacitance across the sensor structure;

(b) at least one temperature-sensitive sensor formed as part of the integrated circuit die, at least one of the at least one temperature-sensitive sensor including:
   (1) a resistance-based temperature-sensitive subcircuit configured to be coupled between a voltage supply and a reference potential, and including a node configured to output a voltage $V_t$ that varies as a function of temperature, the resistance-based temperature-sensitive subcircuit including two resistors configured to be coupled in series between the voltage supply and the reference potential, wherein the node is located between the two resistors; and
   (2) a sample-and-hold circuit having an input coupled to the node of the resistance-based temperature-sensitive subcircuit and configured to output a signal $\Delta T$ indicative of a difference between a first temperature indicated by the voltage $V_t$ at a first time and a second temperature indicated by the voltage $V_t$ at a subsequent second time; and
(d) processing circuitry, coupled to the at least one sensor structure and the at least one temperature-sensitive sensor, the processing circuitry including:
   (1) a capacitance analog-to-digital converter configured to convert a $\Delta C$ analog signal to a corresponding $\Delta C$ digital signal;
   (2) a temperature analog-to-digital converter configured to convert a received analog signal to a corresponding $\Delta T$ digital signal; and
   (3) a digital signal processor, coupled to the capacitance analog-to-digital converter and to the temperature analog-to-digital converter.

2. The integrated circuit die of claim 1, further including at least one heating element positioned sufficiently close to an associated one sensor structure to enable localized heating near the associated one sensor structure.

3. The integrated circuit die of claim 1, further including a pressure sensor die mounted on the surface layer of the integrated circuit die.

4. The integrated circuit die of claim 1, further including at least one environmental sensor for sensing one or more gases and/or one or more vapors, the at least one environmental sensor combined with and coupled to the at least one capacitor structure in a common circuit structure.

5. The integrated circuit die of claim 1, wherein the sensor structure includes an environmentally sensitive dielectric material that is responsive to humidity.

6. The integrated circuit die of claim 1, wherein the sensor structure includes an environmentally sensitive dielectric material that is responsive to a selected biological or chemical molecule.

7. An integrated circuit die including:
(a) at least one capacitor structure formed as part of a surface layer of the integrated circuit die, each capacitor structure including an environmentally sensitive material as a dielectric, the environmentally sensitive material being responsive to a selected environmental characteristic so as to cause a measurable change in electrical capacitance and/or charge across the capacitor structure;
(b) at least one heating element positioned sufficiently close to an associated one capacitor structure of the at least one capacitor structure to enable localized heating near the associated one capacitor structure;
(c) at least one temperature-sensitive sensor formed as part of the surface layer of the integrated circuit die, at least one of the at least one temperature-sensitive sensor including:
   (1) a resistance-based temperature-sensitive subcircuit configured to be coupled between a voltage supply and a reference potential, and a node configured to output a voltage $V_t$ that varies as a function of temperature, the resistance-based temperature-sensitive subcircuit including two resistors configured to be coupled in series between the voltage supply and the reference potential, wherein the node is located between the two resistors; and
   (2) a sample-and-hold circuit having an input coupled to the node of the resistance-based temperature-sensitive subcircuit and configured to output a signal $\Delta T$ indicative of a difference between a first temperature indicated by the voltage $V_t$ at a first time and a second temperature indicated by the voltage $V_t$ at a subsequent second time; and
(d) processing circuitry, coupled to the at least one capacitor structure and the at least one resistance-based temperature-sensitive sensor, the processing circuitry including:
   (1) a capacitance analog-to-digital converter configured to convert a $\Delta C$ analog signal to a corresponding $\Delta C$ digital signal;
   (2) a temperature analog-to-digital converter configured to convert a received analog signal to a corresponding $\Delta T$ digital signal; and
   (3) a digital signal processor, coupled to the capacitance analog-to-digital converter and to the temperature analog-to-digital converter.

8. The integrated circuit die of claim 7, further including a pressure sensor die mounted on the surface layer of the integrated circuit die.

9. The integrated circuit die of claim 7, further including at least one environmental sensor for sensing one or more gases and/or one or more vapors, the at least one environmental sensor combined with and coupled to the at least one capacitor structure in a common circuit structure.

10. The integrated circuit die of claim 7, wherein the sensor structure includes an environmentally sensitive dielectric material that is responsive to humidity.

11. The integrated circuit die of claim 7, wherein the sensor structure includes an environmentally sensitive dielectric material that is responsive to a selected biological or chemical molecule.

12. An integrated circuit die including:
(a) a surface layer;
(b) at least one capacitive sensor structure formed as part of the surface layer, each capacitive sensor structure including an environmentally sensitive dielectric material responsive to a selected environmental characteristic so as to cause a measurable change in electrical capacitance across the capacitive sensor structure;
(c) at least one temperature-sensitive sensor formed as part of the integrated circuit die, at least one of the at least one temperature-sensitive sensor including:
   (1) a resistance-based temperature-sensitive subcircuit configured to be coupled between a voltage supply and a reference potential, and including a node configured to output a voltage $V_t$ that varies as a function of temperature, the resistance-based temperature-sensitive subcircuit including two resistors configured to be coupled in series between the voltage supply and the reference potential, wherein the node is located between the two resistors; and
   (2) a sample-and-hold circuit having an input coupled to the node of the resistance-based temperature-sensitive subcircuit and configured to output a signal ΔT indicative of a difference between a first temperature indicated by the voltage $V_t$ at a first time and a second temperature indicated by the voltage $V_t$ at a subsequent second time; and (d) a capacitance analog-to-digital converter configured to convert a ΔC analog signal to a corresponding ΔC digital signal;

(e) a temperature analog-to-digital converter configured to convert a received analog signal to a corresponding ΔT digital signal; and (f) a digital signal processor, coupled to the capacitance analog-to-digital converter and to the temperature analog-to-digital converter.

13. The integrated circuit die of claim 12, further including a pressure sensor die mounted on the surface layer of the integrated circuit die.

14. The integrated circuit die of claim 12, further including at least one environmental sensor for sensing one or more gases and/or one or more vapors, the at least one environmental sensor combined with and coupled to the at least one capacitor structure in a common circuit structure.

15. The integrated circuit die of claim 12, wherein the environmentally sensitive dielectric material is responsive to humidity.

16. The integrated circuit die of claim 12, wherein the environmentally sensitive dielectric material is responsive to a selected biological or chemical molecule.

17. The integrated circuit die of claim 12, further including at least one heating element positioned sufficiently close to an associated one capacitive sensor structure to enable localized heating near the associated one capacitive sensor structure.

\* \* \* \* \*